(12) United States Patent
Kweon et al.

(10) Patent No.: US 12,138,401 B2
(45) Date of Patent: Nov. 12, 2024

(54) APPARATUS AND METHOD FOR EVALUATING PROCEEDING ROUTE OF GUIDE WIRE

(71) Applicant: LN ROBOTICS INC., Seoul (KR)

(72) Inventors: Jihoon Kweon, Seoul (KR); Young Hak Kim, Seoul (KR); June Goo Lee, Seoul (KR); Young Jin Moon, Seoul (KR); Jaesoon Choi, Seoul (KR)

(73) Assignee: LN ROBOTICS INC., Seoul (KR)

( * ) Notice: Subject to any disclaimer, the term of this patent is extended or adjusted under 35 U.S.C. 154(b) by 443 days.

(21) Appl. No.: 17/603,743

(22) PCT Filed: Apr. 2, 2020

(86) PCT No.: PCT/KR2020/004495
§ 371 (c)(1),
(2) Date: Oct. 14, 2021

(87) PCT Pub. No.: WO2020/222429
PCT Pub. Date: Nov. 5, 2020

(65) Prior Publication Data
US 2022/0193369 A1 Jun. 23, 2022

(30) Foreign Application Priority Data
Apr. 30, 2019 (KR) .................... 10-2019-0050785

(51) Int. Cl.
*G06T 7/73* (2017.01)
*A61B 34/10* (2016.01)
(Continued)

(52) U.S. Cl.
CPC ......... *A61M 25/0105* (2013.01); *A61B 34/10* (2016.02); *G06T 7/73* (2017.01);
(Continued)

(58) Field of Classification Search
CPC ................................................ A61M 25/0105
See application file for complete search history.

(56) References Cited

U.S. PATENT DOCUMENTS

| 7,203,534 B2 | 4/2007 | Mollus et al. |
| 8,374,689 B2 | 2/2013 | Gopinathan et al. |

(Continued)

FOREIGN PATENT DOCUMENTS

| JP | 2003-245273 A | 9/2003 |
| JP | 6433745 B2 | 12/2018 |

(Continued)

OTHER PUBLICATIONS

International Search Report issued on Jul. 8, 2020 in PCT/KR2020/004495 filed Apr. 2, 2020, 3 pages.

(Continued)

*Primary Examiner* — Oneal R Mistry
(74) *Attorney, Agent, or Firm* — Oblon, McClelland, Maier & Neustadt, L.L.P.

(57) ABSTRACT

The present invention relates to an image processing system for a catheter operation. One embodiment comprises: a storage unit for at least temporarily storing a plurality of candidate routes on which a guide wire can proceed on a changing route caused by vascular bifurcations while proceeding from a first point by using a blood vessel image; and a processor for selecting, from an image inputted while an operation proceeds, at least one route corresponding to the current shape of the guide wire on the basis of a similarity comparison between the current shape of the guide wire and each of the plurality of candidate routes.

8 Claims, 5 Drawing Sheets

(51) Int. Cl.
*A61M 25/01* (2006.01)
*A61M 25/09* (2006.01)

(52) U.S. Cl.
CPC ............... *A61B 2034/107* (2016.02); *A61M 2025/0166* (2013.01); *A61M 25/09041* (2013.01); *G06T 2207/30101* (2013.01)

(56) References Cited

U.S. PATENT DOCUMENTS

| | | | |
|---|---|---|---|
| 8,494,794 | B2 | 7/2013 | Dutta et al. |
| 8,798,712 | B2 | 8/2014 | Gopinathan et al. |
| 8,825,151 | B2 | 9/2014 | Gopinathan et al. |
| 9,675,276 | B2 | 6/2017 | Gopinathan et al. |
| 10,548,669 | B2 | 2/2020 | Goyal |
| 10,932,815 | B1* | 3/2021 | Lenker ............... A61B 17/3468 |
| 2010/0106149 | A1* | 4/2010 | Habib ................. A61B 18/082 |
| | | | 606/28 |
| 2010/0312100 | A1* | 12/2010 | Zarkh ...................... G06T 7/32 |
| | | | 382/128 |
| 2011/0264075 | A1* | 10/2011 | Leung .................... A61B 18/20 |
| | | | 607/116 |
| 2012/0101369 | A1 | 4/2012 | Patil et al. |
| 2013/0123694 | A1 | 5/2013 | Subramaniyan et al. |
| 2014/0032142 | A1 | 1/2014 | Dutta et al. |
| 2014/0142398 | A1 | 5/2014 | Patil et al. |
| 2017/0332945 | A1 | 11/2017 | Gopinathan et al. |
| 2020/0129740 | A1* | 4/2020 | Kottenstette ........... A61B 34/30 |
| 2020/0305970 | A1* | 10/2020 | Ben-Haim ........... A61B 5/6852 |
| 2023/0145569 | A1* | 5/2023 | McWeeney ....... A61M 25/0662 |
| | | | 600/109 |

FOREIGN PATENT DOCUMENTS

| | | |
|---|---|---|
| JP | 2019-10533 A | 1/2019 |
| JP | 2019-510547 A | 4/2019 |
| KR | 10-0466409 B1 | 1/2005 |
| KR | 10-2015-0025461 A | 3/2015 |
| KR | 10-1512110 B1 | 4/2015 |
| KR | 10-1549528 B1 | 9/2015 |
| KR | 10-2018-0016687 A | 2/2018 |

OTHER PUBLICATIONS

Coronary Angiography, Nucleus Medical Media, 2012, https:/www.youtube.com/watch?v=GhNT2GifkJg, 1 total page.

* cited by examiner

APPARATUS AND METHOD FOR EVALUATING PROCEEDING ROUTE OF GUIDE WIRE

TECHNICAL FIELD

The following description relates to a procedure method and apparatus. More particularly, the following description relates to a method and apparatus to evaluate an intravascular proceeding route of a guidewire used for a catheter procedure.

BACKGROUND ART

A remote control robot system has been developed to insert a catheter more precisely and accurately and to remove a radiation exposure risk in case of taking an X-ray during a procedure to identify a position of an inserted procedure equipment during an interventional procedure using a catheter to treat a cardiovascular or a peripheral vascular disease.

It is tremendously difficult to transfer a guidewire to a target point along numerous blood vessels of a human body. In addition, a blood vessel route may be temporarily identified by injecting contrast media. However, a duration of showing is approximately 3 seconds and except for that, a practitioner may insert a guidewire to a target point while viewing a shape of the guidewire only. Thus, there is a desire for a development of a system to identify a current intravascular position using a shape of a guidewire or navigate a route.

DISCLOSURE OF THE INVENTION

Technical Solutions

According to an aspect, there is provided an image processing system for a catheter procedure, the system including a storage unit to at least temporarily store a plurality of candidate routes on which a guidewire is to proceed from a first point as a route is changed by vascular bifurcation points, using a blood vessel image; and a processor configured to select at least one route corresponding to a current shape of the guidewire based on a comparison of similarities between the current shape of the guidewire and each of the plurality of candidate routes, from an image input during the procedure.

The processor may be configured to evaluate and provide a probability of a match between the current guidewire and each of the plurality of candidate routes.

The probability of the match may be generated by calculating and comparing correlation information between the guidewire and each of the plurality of candidate routes.

The processor may be configured to exclude at least one route with low similarity from the plurality of candidate routes.

In addition, the processor may be configured to correct the similarity referring to a blood vessel image captured while the system is in operation.

The plurality of candidate routes may include at least one of a blood vessel connecting an entry point of the guidewire to a target point or a blood vessel adjacent to the connecting blood vessel.

The processor may be configured to determine the similarity considering a deformable shape of the guidewire within the width of a blood vessel of each of the plurality of candidate routes.

According to another aspect, there is provided an image processing method for a catheter procedure including storing a plurality of candidate routes on which a guidewire proceeds from a first point using a blood vessel image wherein a route is changed by a vascular bifurcation point; comparing similarities between a current shape of the guidewire and the plurality of candidate routes from an image input during the procedure; and selecting at least one route corresponding to the current shape of the guidewire based on the comparing.

BEST MODE FOR CARRYING OUT THE INVENTION

Figure 1:
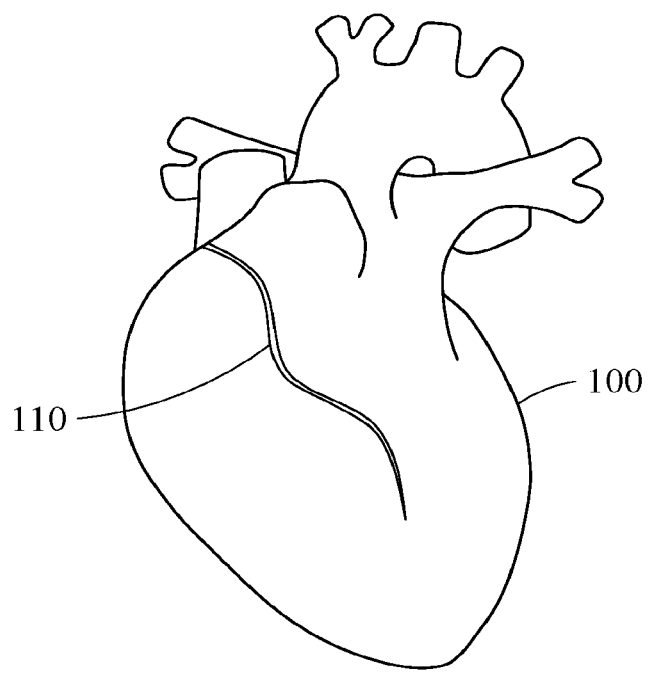
FIG. 1 is a diagram illustrating a heart and a guidewire placed inside of a blood vessel of the heart according to an example embodiment.

Hereinafter, the example embodiments will be described in detail with reference to the accompanying drawings. The scope of the right, however, should not be construed as limited to the example embodiments set forth herein. In the drawings, like reference numerals are used for like elements.

The terms used herein are selected from terms generally understood by those skilled in the related art, but may have different meanings according to technical developments and/or changes, practices, and preferences of an engineer. Accordingly, the terms used herein should not be construed as limiting the technical spirit, and should be construed as illustrative terms to describe example embodiments.

In addition, in a specific case, most appropriate terms are arbitrarily selected by the applicant. In this instance, the meanings of the arbitrarily used terms will be clearly explained in the corresponding description. Hence, the terms should be understood not by the simple names of the terms but by the meanings of the terms and the following overall description of this specification.

FIG. 1 is a diagram illustrating a heart and a guidewire placed inside of a blood vessel of the heart according to an example embodiment. FIG. 1 illustrates a guidewire 110 and a heart 100 shown in an X-ray image used for a cardiovascular procedure.

A practitioner who inserts the guidewire 110 may transfer the guidewire 110 to a target point while watching an X-ray image as shown in FIG. 1. For example, in case of a cardiovascular procedure, a practitioner may begin to insert a guidewire near a thigh and transfer the guidewire to a heart along a blood vessel. The practitioner may have a difficulty in identifying a blood vessel route and may have to determine based on only a shape of the guidewire whether the guidewire is properly proceeding.

Figure 2:
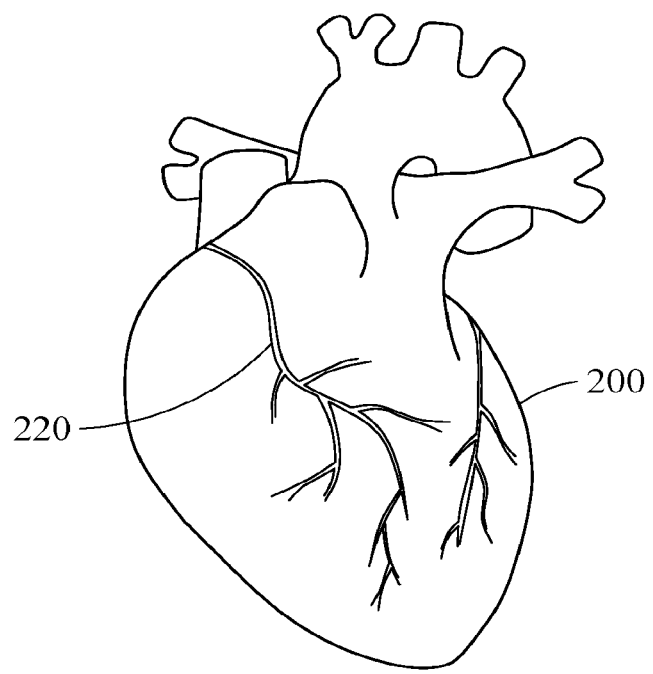
FIG. 2 is a diagram illustrating blood vessels of a heart shown when contrast media are injected according to an example embodiment.

During the process, an aspect of the blood vessel may be temporarily identified by injecting contrast media near the guidewire. Referring to FIG. 2, an aspect of a blood vessel route 220 of a heart 200 identified at a moment of injecting contrast media is illustrated.

However, even if the contrast media are injected, an image as shown in FIG. 2 may not be continuously shown. The image may be confirmed only temporarily. Specifically, the contrast media may be spread throughout a body by blood ejected from a heart, and the contrast media may be all scattered within two seconds at the shortest and five seconds at the longest. Thus, a route may not be identified.

That is, the blood vessel route 220 may be instantaneously identified. However, since a duration of showing the blood vessel route 220 may be approximately three seconds, except for the duration, the practitioner may have to insert the guidewire 110 to a target point depending on a shape of the guidewire 110 along the blood vessel route 220 based on a memory of the practitioner. In addition, in a real procedure, it may be more difficult to identify a location of a blood vessel since the guidewire 110 and the heart 100, 200 are moving due to cardiac impulse and so forth.

In case of using a lot of contrast media during a process of inserting the guidewire, since a side effect may occur to a recipient (a patient), an injection of contrast media may need to be minimized. Thus, there is a demand for an image processing system which allows a practitioner or a mechanical apparatus to insert a guidewire smoothly to a target point while minimizing an injection of contrast media.

According to an example embodiment, there is provided an image processing system for a catheter procedure, the system including a storage unit to at least temporarily store a plurality of candidate routes on which a guidewire is to proceed from a first point as a route is changed by vascular bifurcation points, using a blood vessel image; and a processor configured to select at least one route corresponding to a current shape of the guidewire based on a comparison in a similarity between the current shape of the guidewire and each of the plurality of candidate routes, from an image input during the procedure.

Figure 3:
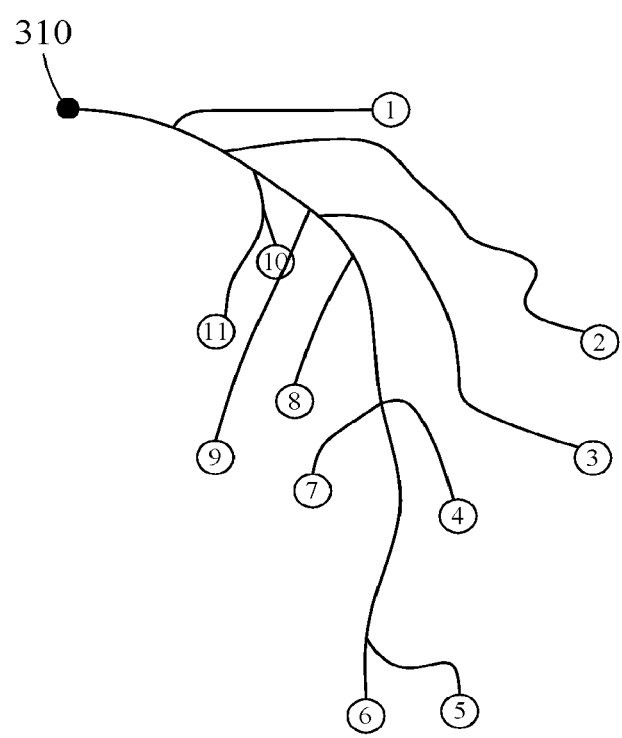
FIG. 3 is a diagram illustrating a first point and blood vessel candidate routes according to an example embodiment.

Referring to FIG. 3, a blood vessel candidate route corresponding to a first point 310 is illustrated according to an example embodiment. The storage unit may at least temporarily store a plurality of candidate routes (①through ⑪) on which a guidewire is to proceed from the first point 310 as a route is changed by vascular bifurcation points, as shown in FIG. 3. For example, the first point 310 may be set to any one location of an inlet of a blood vessel or a catheter tip, but is not limited thereto.

The plurality of candidate routes may refer to at least one of a blood vessel connecting an entry point of the guidewire to a target point or a blood vessel adjacent to the connecting blood vessel.

The candidate routes may be extracted from an image of a blood vessel captured before a procedure by using contrast media in advance, and stored. That is, in case of a procedure which requires an insertion of a guidewire, an image of a blood vessel is obtained in advance and then, with a predetermined point as the first point 310, a plurality of candidate routes (①through ⑪) which may be proceedable from the first point may be found and stored.

FIG. 3 is a diagram illustrating eleven candidate routes as a non-limiting example. A guidewire may move forward from the first point 310 as a base and proceed along any one of the eleven candidate routes.

As described in FIG. 1, a practitioner may determine whether the guidewire is properly proceeding depending only on the shape of the guidewire while in a state that blood vessel candidate routes are not visible. On the other hand, an image processing system for a catheter procedure according to an example embodiment may find and select the most similar route among candidate routes stored based on the shape of the guidewire.

Using a travel distance of the guidewire from the first point 310 and the shape of the guidewire, a position where the guidewire is currently located in a blood vessel may be determined.

In addition, a blood vessel which is most similar to the shape of the guidewire may be determined as the blood vessel in which the guidewire is currently located.

For example, when a guidewire has to proceed along a blood vessel ⑥ among the blood vessel candidate routes, if the guidewire is located in the blood vessel ⑥, it may be determined that the guidewire is properly proceeding. If the guidewire strays out of the blood vessel ⑥ and proceeds toward a blood vessel ③, it may be determined that the guidewire is proceeding in a wrong way.

According to another embodiment, the image processing system for a catheter procedure may evaluate and provide a probability of a match of a current guidewire to each of a plurality of candidate routes.

For example, but not limited to, a probability of a match of a current shape of a guidewire to each of the eleven candidate routes may be evaluated as 10% for a route ①, 15% for a route ②, and 95% for a route ⑥. The probability of the match may be generated by calculating and comparing correlation information between the guidewire and each of the plurality of candidate routes.

According to another embodiment, the image processing system may exclude at least one route with a low similarity from the plurality of candidate routes.

For example, if a guidewire is currently passing by a branch point of the routes ② and ⑥, a similarity to a route ①, which may be entered from the previous branch point, may be considered as substantially low. Thus, the route ① may be excluded from the candidate routes.

Alternatively, if the guidewire reached a branch point of routes ⑤ and ⑥, all previous routes except for the two routes, may be excluded from the candidate routes.

The image processing system may correct the similarity referring to a blood vessel image captured while the system is in operation. The processor, for determining a similarity between a shape of a guidewire and the candidate routes by a previously obtained image of a blood vessel, may correct the similarity by additionally using an image of a blood vessel captured during a procedure.

Specifically, since an image of a blood vessel captured during a procedure and candidate routes before the procedure at a point in time of being stored in the storage unit may have a difference in time, a similarity may be corrected using a recent image of the blood vessel captured during the procedure.

In addition, the image processing system may correct a similarity using a displacement between an image of a blood vessel obtained previously and an image of the blood vessel captured during a procedure. For example, the image processing system may calculate a displacement between positions of a catheter tip in the two images of a blood vessel and correct the similarity using the calculated displacement. The displacement of the catheter tip in the image of the blood vessel may be caused by respiration of a patient. This may be because an organ such as a heart may be moved by a diaphragm during respiration, and the catheter may also be moved in the image.

According to another example embodiment, the image processing system may also determine a similarity to a shape of a guidewire considering a width of a blood vessel.

Figure 4A:
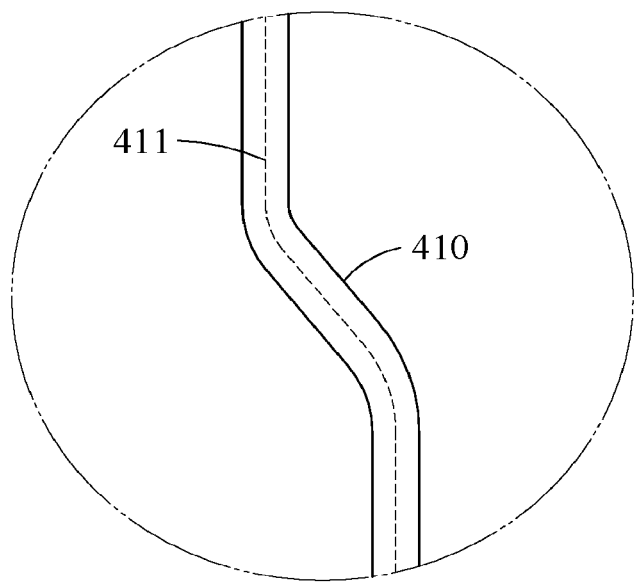
FIG. 4 illustrates guidewires which may be deformed corresponding to a width of a blood vessel according to an example embodiment.
Figure 4B:
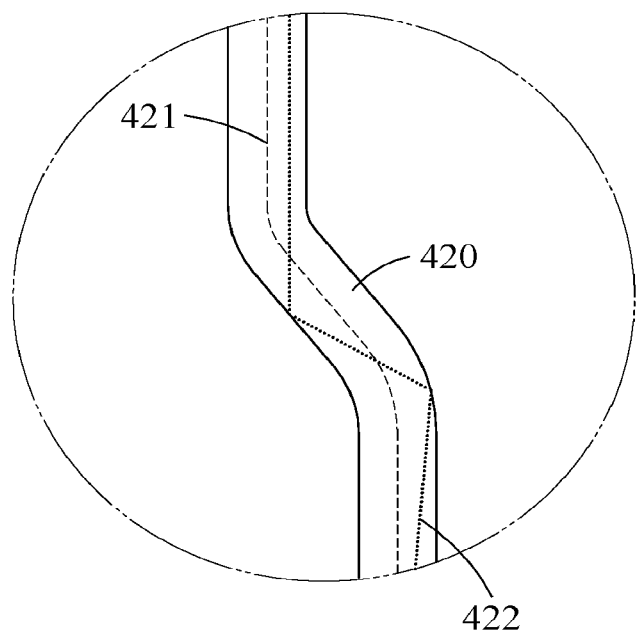

FIG. 4 illustrates guidewires which may be deformed corresponding to a width of a blood vessel according to an example embodiment. FIG. 4A illustrates a route 411 of a guidewire in a narrow blood vessel 410, and FIG. 4B illustrates routes 421 and 422 of a guidewire in a wide blood vessel 420.

A width or a thickness of a blood vessel may refer to an inside diameter of the blood vessel in three-dimensions, and in case of displayed in a two-dimensional drawing, may refer to a perpendicular distance to a length direction of the blood vessel.

To describe in detail, in FIG. 4A, since the blood vessel 410 is narrow in width, a guidewire may have difficulties in deforming inside of the blood vessel 410, and the route 411 of the guidewire may be formed as substantially similar to a shape of the blood vessel. That is, the guidewire may move along the shape of the blood vessel.

On the other hand, referring to FIG. 4B, since a width of the blood vessel 420 is wider than a thickness of a guidewire, the guidewire may move in various ways within the width of the blood vessel. For example, a guidewire may move along the route 421 which is similar to a shape of the blood vessel, and in another example embodiment, a guidewire may move along the route 422 which has a slightly different form while bumping against a wall of a blood vessel.

Thus, the processor may determine the similarity considering a deformable shape of a guidewire corresponding to the width of the blood vessel within the width of the blood vessel. If a width of a blood vessel is narrow, when a shape of a guidewire is substantially similar to a candidate route, a similarity may be determined as high. Conversely, if a width of a blood vessel is wide, even though a shape of a guidewire is slightly different from a candidate route but is still deformable within the width of the blood vessel, a similarity may be determined as high.

Consequently, a similarity may be corrected corresponding to a width of a blood vessel when determining similarities with respect to a plurality of candidate routes.

Figure 5:
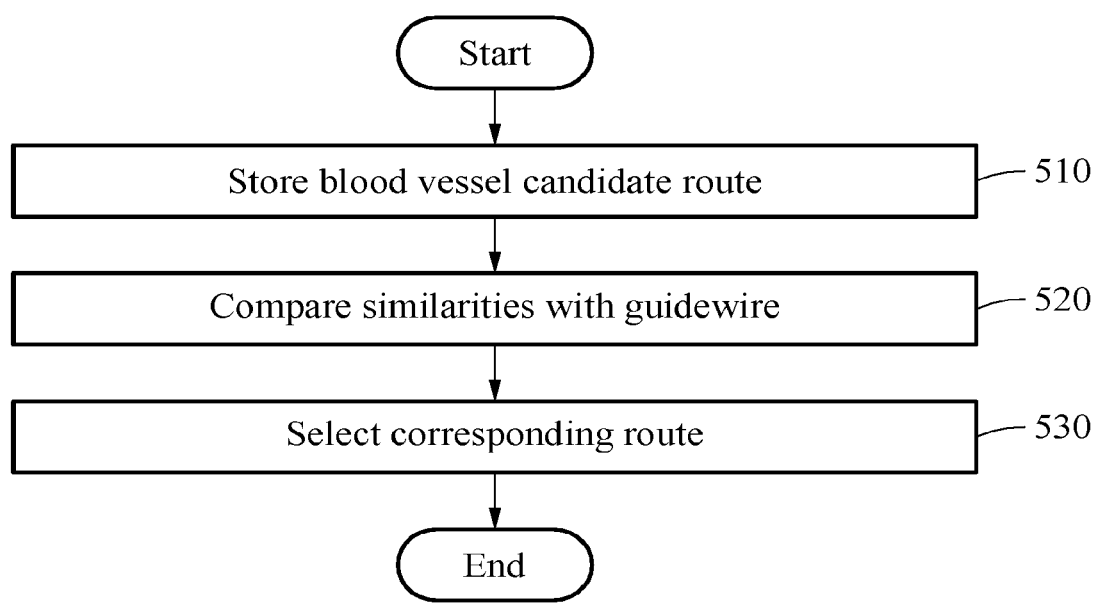
FIG. 5 illustrates an evaluation method of a proceeding route of a guidewire according to an example embodiment.

FIG. 5 illustrates an evaluation method of a proceeding route of a guidewire according to an example embodiment. FIG. 5 is a flowchart sequentially illustrating the evaluation method for a proceeding route of a guidewire performed by an image processing system.

The evaluation method for a proceeding route of a guidewire may include operation 510 of storing blood vessel candidate routes, operation 520 to compare similarities to the guidewire and operation 530 to select a corresponding route.

Operation 510 of storing blood vessel candidate routes may be an operation of at least temporarily storing a plurality of candidate routes on which a guidewire is to proceed from a first point as a route is changed by vascular bifurcation points, using a blood vessel image.

Here, the plurality of candidate routes may include at least one of a blood vessel connecting an entry point of the guidewire to a target point or a blood vessel adjacent to the connecting blood vessel. For example, if a guidewire enters from a thigh and moves to a brain, a blood vessel connecting a blood vessel of the thigh from which the guidewire enters and a brain vessel, and a blood vessel adjacent to the corresponding vessel may be stored as candidate routes.

The plurality of candidate routes may be at least temporarily stored, and both of permanently stored or temporarily stored method may be possible.

Operation 520 of comparing similarities to a guidewire may be an operation of comparing similarities between a current shape of the guidewire and the plurality of candidate routes from an image input during the procedure.

Specifically, similarities may be compared using a shape (form) and a depth of an insertion of a guidewire. As long as a guidewire does not perforate a blood vessel, the guidewire may move only inside of the blood vessel. Thus, considering a depth of an insertion of the guidewire, a reachable point for the guidewire within a blood vessel may exist. In addition, a shape of the guidewire may be compared to each of the plurality of candidate routes.

In addition, in operation of comparing similarities, a probability of a match between a current guidewire and each of the plurality of candidate routes may be calculated. The probability of the match may be calculated by calculating and comparing correlation information between the current guidewire and each of the plurality of candidate routes.

Operation 530 of selecting a corresponding route may be an operation of selecting at least one route corresponding to a current shape of the guidewire based on the comparison of similarities performed in operation 520.

The probability of the match and/or the similarity to each of the candidate routes may be calculated, and based on the similarities, the most similar candidate route to the current shape of the guidewire may be selected as a corresponding route to the current guidewire.

According to another embodiment, since the probability of the match and/or the similarities to each of the candidate routes may be determined, a route with a similarity that exceeds a predetermined level to each of the candidate routes may be selected as a corresponding route to the current guidewire. That is, in accordance with levels of similarities, a plurality of routes may be selected as routes corresponding to the current guidewire.

Consequently, the image processing system for a catheter procedure may find the most corresponding route to the current guidewire. Accordingly, it may be determined whether the guidewire is properly inserted.

In addition, using the image processing system may allow a practitioner to select whether to proceed or change a route by immediately determining a proceeding route during a procedure and delivering the determined proceeding route to the practitioner, and reduce control time or a number of control commands when using a machine system.

In addition, although FIGS. 1 and 2 mainly describe with heart and blood vessels as a non-limiting example, the same principle may be applied to various blood vessels such as heart and blood vessels, brain vessels and peripheral blood vessels.

The units described herein may be implemented using a hardware component, a software component and/or a combination thereof. A processing device may be implemented using one or more general-purpose or special purpose computers, such as, for example, a processor, a controller and an arithmetic logic unit (ALU), a DSP, a microcomputer, an FPGA, a programmable logic unit (PLU), a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, to independently or uniformly instruct or configure the processing device to operate as desired. Software and data may be embodied permanently or temporarily in any type of machine, component, physical or pseudo equipment, computer storage media or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording medias.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher-level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

The invention claimed is:

1. An image processing system for a catheter procedure, the system comprising:
a memory to at least temporarily store a plurality of candidate routes on which a guidewire is to proceed from a first point as a route is changed by vascular bifurcation points, using a blood vessel image; and
a processor configured to select at least one route corresponding to a current shape of the guidewire based on a comparison of similarities between the current shape of the guidewire and each of the plurality of candidate routes, from an image input during the catheter procedure, wherein
the processor is configured to evaluate and provide a probability of a match between the guidewire and each of the plurality of candidate routes, the probability of the match being generated by calculating and comparing correlation information between the guidewire and each of the plurality of candidate routes.

2. The system of claim 1, wherein the processor is configured to exclude at least one route with low similarity from the plurality of candidate routes.

3. The system of claim 1, wherein the processor is configured to correct the similarity referring to a blood vessel image captured while the system is in operation.

4. The system of claim 1, wherein the plurality of candidate routes comprises at least one of a blood vessel connecting an entry point of the guidewire to a target point or a blood vessel adjacent to the connecting blood vessel.

5. The system of claim 1, wherein the processor is configured to determine the similarity considering a deformable shape of the guidewire within a width of a blood vessel of each of the plurality of candidate routes.

6. An image processing method for a catheter procedure comprising:
storing, in a memory, a plurality of candidate routes on which a guidewire proceeds from a first point using a blood vessel image wherein a route is changed by a vascular bifurcation point;
comparing, by a processor, similarities between a current shape of the guidewire and the plurality of candidate routes from an image input during the catheter procedure; and
selecting, by the processor, at least one route corresponding to the current shape of the guidewire based on the comparing, wherein
the method further comprises evaluating and providing a probability of a match between the guidewire and each of the plurality of candidate routes, the probability of the match being generated by calculating and comparing correlation information between the guidewire and each of the plurality of candidate routes.

7. A non-transitory computer-readable storage medium including computer executable instructions, wherein the instructions, when executed by a computer, cause the computer to perform a method for a catheter procedure, the method comprising:
storing a plurality of candidate routes on which a guidewire proceeds from a first point using a blood vessel image wherein a route is changed by a vascular bifurcation point;
comparing similarities between a current shape of the guidewire and the plurality of candidate routes from an image input during the catheter procedure; and
selecting at least one route corresponding to the current shape of the guidewire based on the comparing, wherein
the method further comprises evaluating and providing a probability of a match between the guidewire and each of the plurality of candidate routes, the probability of the match being generated by calculating and comparing correlation information between the guidewire and each of the plurality of candidate routes.

8. The system of claim 1, wherein the plurality of candidate routes were extracted from a previous blood vessel image captured before the catheter procedure using contrast media.

* * * * *